United States Patent [19]

Erdrich et al.

[11] Patent Number: 5,618,372

[45] Date of Patent: Apr. 8, 1997

[54] PROCESS FOR THE PRODUCTION OF A FIRMLY ADHERING, MOISTURE-PROOF COATING OF PLASTIC ON A SUBSTRATE

[75] Inventors: Albert Erdrich, Bad Nauheim; Sonja Fremdt, Weinbach; Steffen Oppawsky, Bad Homburg, all of Germany

[73] Assignee: Heraeus Kulzer GmbH, Hanau, Germany

[21] Appl. No.: 559,742

[22] Filed: Nov. 15, 1995

[30] Foreign Application Priority Data

Nov. 18, 1994 [DE] Germany .......... 44 41 124.3

[51] Int. Cl.$^6$ ................. B05D 1/38; B05D 3/02
[52] U.S. Cl. .......... 156/310; 156/315; 427/2.26; 427/207.1; 427/378; 427/379; 427/388.4; 427/389.7; 427/393.5; 427/393.6; 427/407.2; 427/409; 427/412.1
[58] Field of Search ............... 427/2.26, 207.1, 427/378, 379, 388.4, 389.7, 393.5, 393.6, 407.2, 409, 412.1; 156/310, 315

[56] References Cited

U.S. PATENT DOCUMENTS

| 5,418,262 | 5/1995 | Göbel ................ 523/116 |
| 5,548,001 | 8/1996 | Podszum et al. ........ 523/116 |

FOREIGN PATENT DOCUMENTS

| 0591716 | 4/1994 | European Pat. Off. . |
| 4228530 | 6/1993 | Germany . |
| 4010176 | 10/1996 | Germany . |
| 33940 | 1/1955 | Switzerland . |

*Primary Examiner*—Shrive Beck
*Assistant Examiner*—Erma Cameron
*Attorney, Agent, or Firm*—Felfe & Lynch

[57] ABSTRACT

A process for the production of a firmly adhering, moisture-proof coating of plastic on a substrate of metal, ceramic, glass, or polymer by the application of a liquid preparation containing water, solvent, a (meth)acrylate, and a reactive polymer and by solidifying this coating by heating it to a temperature above 100° C. is described. A first preparation is applied to the substrate and at least partially dried; a second preparation is then applied to the partially dried first preparation and at least partially dried. Then the coating is heated to a temperature in the range of 150°–400° C. to solidify it.

The first preparation contains:

- 5–25 wt. % of an aqueous copolymer suspension, the copolymer consisting of a mixture of 40–80 wt. % of acrylonitrile and 60–20 wt. % of butyl acrylate;
- 5–20 wt. % of water;
- 35–75 wt. % of a polar solvent; and
- 3–15 wt. % of a (meth)acrylate which is nonvolatile at temperatures of up to 250° C., with the provision that the percentages always add up to 100%;

and the second preparation contains:

- 5–20 wt. % of a 40–90 wt. % solution of an isocyanate group-free polyurethane baking resin in solvent naphtha 100;
- 65–85 wt. % of solvent; and
- 3–20 wt. % of a (meth)acrylate which is nonvolatile at temperatures of up to 250° C., with the provision that the percentages always add up to 100%.

20 Claims, No Drawings

PROCESS FOR THE PRODUCTION OF A FIRMLY ADHERING, MOISTURE-PROOF COATING OF PLASTIC ON A SUBSTRATE

The present invention pertains to a process for the production of a firmly adhering, moisture-proof coating of plastic on a substrate of metal, ceramic, glass, or polymer by the application of a liquid preparation containing water, solvent, a (meth)acrylate (i.e., a methacrylate or an acrylate), and a reactive polymer, and by the consolidation of this coating by heating it to a temperature above 100° C.

The invention also pertains to the use of the coating produced according to the process.

A process such as this is known from DE-A1 4,228,530. This document describes a firmly adhering, water-impermeable, and hydrolysis-resistant bonding layer for the bonding of metal, ceramic, glass, and polymer to plastic and a dispersion for their production. This bonding layer is produced from a phenol-formaldehyde dispersion. For this purpose, two dispersions are prepared separately first, and these two dispersions are then mixed together to form a liquid preparation, which is applied to a substrate. The applied preparation is then given a heat treatment at 120°–220° C. for 15 minutes. One of the dispersions of the preparation consists essentially of a phenol-formaldehyde dispersion, whereas the other dispersion contains one or more olefinic unsaturated, mono- or multifunctional methacrylate compounds. It has been found that, when this preparation is used as a bonding agent between metal and plastic, relatively high adhesion values can be obtained after the adhesive has fully cured. A certain disadvantage of this preparation or of the individual dispersions, however, is that they are stable for only a short period of time. That is, they are stable for usage for only 2–3 months during storage, which is not adequate for commercial use. In addition, the storage stability also depends on the specific storage conditions; that is, to achieve even a merely acceptable storage stability time, the dispersions or the preparation must be stored under refrigeration. In addition, one of the dispersions of the preparation contains phenol as well as formaldehyde, both of which are dangerous to human health. Although these substances are crosslinked to a certain extent in the cured preparation, it has not yet been demonstrated that the crosslinking is complete. It therefore cannot be completely excluded that formaldehyde is able to escape by evaporation.

Proceeding from the state of the art described above, the present invention is based on the task of creating a process for the production of a firmly adhering, moisture-proof coating of plastic, according to which high adhesion values are obtained, especially in the case of metal-to-plastic bonds; no health-endangering substances are used; and there are no problems with storage stability.

The task described above is accomplished by means of a process for the production of a firmly adhering, moisture-proof coating of plastic on a substrate of metal, ceramic, glass, or polymer by the application of a liquid preparation containing water, acetone, a (meth)acrylate, and a reactive polymer and by the consolidation of this coating by heating it to a temperature of more than 100° C., which is characterized in that a first preparation is applied to the substrate and allowed to dry at least partially; in that a second preparation is applied to the partially dried first preparation and allowed to dry at least partially; and in that the coating is then consolidated by heating it to a temperature in the range of 150°–400° C., where the first preparation contains:

5–25 wt. % of an aqueous copolymer suspension, the copolymer consisting of a mixture of 40–80 wt. % of acrylonitrile and 60-20 wt. % of butyl acrylate;

5–20 wt. % of water;

35–75 wt. % of a polar solvent; and

3–15 wt. % of a (meth)acrylate which is nonvolatile at temperatures of up to 250° C., with the provision that the percentages always add up to 100%; and where the second preparation contains:

5–20 wt. % of a 40–90 wt. % solution of an isocyanate group-free polyurethane baking resin in solvent naphtha 100;

65–85 wt. % of solvent; and

3–20 wt. % of a (meth)acrylate which is nonvolatile at temperatures of up to 250° C., with the provision that the percentages always add up to 100%.

When the special first preparation and the special second preparation of the system are applied successively to a carrier and then subjected to a temperature treatment, a coating is obtained which offers a permanent, moisture-stable, non-gapping, and extremely strong bond to a substrate of metal, ceramic, glass, or polymer. It has also been found that the two preparations used are stable for long periods of time under normal room conditions; that is, there is no need to take special measures to keep a supply of these preparations on hand.

The bonding principle is based on the sequential buildup of the system layers and on the continuous change in the mechanical properties from the substrate to the plastic or adhesive. Whereas the straightforwardly melting polyacrylonitrile/butyl acrylate copolymer shares some of the hard and tough properties of the substrate, the crosslinking polyurethane baking resin tends to be tough and elastic. Because it is able to undergo a certain amount of deformation, it absorbs a certain amount of the forces coming from the outside and thus transmits only a portion of these forces to the boundary layer between the two layers of the preparation. At the same time, the two resin systems are crosslinked to such a high degree both in themselves and with each other that it is virtually impossible for moisture to penetrate as far as this boundary layer.

The essential point of the process according to the invention is that the system is built up of the two special preparations, which are applied in succession in such a way that, before the second preparation is applied, the first preparation is allowed to solidify on the substrate to such an extent that the second preparation can be applied to the first preparation with essentially no mixing between the two. The entire system is then subjected to a curing process by heating it to a temperature in the range of 150°–400° C. Extensive tests have also shown that there is no need to impose strict requirements on the processing work as far as the cleanness of the substrate surfaces is concerned. According to the known processes, the substrate must be pretreated by chemical cleaning or sandblasting, for example, to ensure that reproducible results are obtained. With the system according to the invention, however, the adhesive strength values which are obtained in the case of clean surfaces have not been found to vary significantly from those obtained on surfaces contaminated to a certain degree with grease, for example. The strength of the bond, regardless of the quality of the surface, is at the very least sufficient to achieve the adhesion values required in engineering for metal-to-plastic bonds and especially to achieve the values required in the field of dentistry. Nevertheless, a cleaning step can offer a certain advantage in the sense that the adhesion values will be increased. Adhesive strength values of up to 40 MPa can be obtained with the process and the preparations according to the invention; the strength of the bond remains virtually unchanged even after being subjected to alternating thermal stress in water at 5°/55° C. over the course of 5,000 cycles. In addition, no microscopic gaps between the layers can be found.

The first preparation to be applied is preferably one which contains a suspension of an acrylonitrile/butyl acrylate copolymer with a solids content of 30–50 wt. %. If, as is preferred, a copolymer of 60 wt. % of acrylonitrile and approximately 40 wt. % of butyl acrylate is used as the copolymer in the mixture of the first preparation, a plastic coating with good adhesion values will be obtained.

In a further modification, the second preparation contains an approximately 75 wt. % solution of an isocyanate group-free polyurethane baking resin in solvent naphtha 100.

With respect to the requirements of the solvent selected for use in the first preparation in particular, a polar solvent should be used. It is preferable to use ethanol or isopropanol as the polar solvent. It is even more preferable, however, to use acetone, because acetone evaporates relatively quickly and therefore makes it possible to achieve good preliminary drying of the first preparation before the second preparation is applied. The time it takes for the first preparation to predry before the second preparation is applied is in the range of approximately 1–2 minutes. Sufficient partial drying of the first preparation before the application of the second preparation can be easily determined visually by the user, because the layer changes in appearance from dark and wet to dry and whitish.

The preferred thicknesses in which the layers of the first and second preparations are applied are in the range of 1–10 µm, and preferably in the range of 4–8 µm. It is easy to apply layers of this thickness by the use of a brush. The consistency of the first preparation is adjusted with water in such a way that the water content of this preparation is preferably in the range of 14–18 wt. %. If too much water is present, the preparation will not be stable. Whereas the predrying of the first preparation can occur in air, which is also true for the predrying of the second preparation, the subsequent complete curing of the applied layers is carried out under the effect of heat. For parts with large surface areas which are to be coated with a plastic coating of the type described here, a heating oven has been found to be suitable, in which the specified curing temperature, which is preferably in the range of 200°–400° C., can be maintained.

For the thermal curing of the applied preparations, it has been found that an essential criterion is the transition temperature of the curing reaction. This transition temperature is approximately 170° C. Only after the as yet-unsolidified coating has been held for a certain minimum period of time at this temperature does the curing reaction begin, which leads to the complete curing and hardening of the coating. Only in this way can the adhesion values described above be achieved. The oven in which the part to be cured is introduced should be set at an isothermal curing temperature in the range of 160°–220° C., and preferably in the range of 180°–200° C., and should be held at the specified temperature for 1–10 minutes, and preferably for 2–4 minutes. This temperature can be set with great precision and maintained for the indicated period of time in an oven. In this way it can be guaranteed that the coating will be heated under isothermal conditions.

Especially when small components are to be provided according to the process of the invention with a coating of this type or with a corresponding bonding layer formed from such a coating, it has been found advantageous to conduct the curing process with a stream of hot air. When a stream of hot air is used, it is possible to apply heat in a defined manner to specific areas of small components, including those with complicated shapes. In such a case, the temperature of the hot air stream is preferably set at 300°–350° C. and applied for approximately 10–25 seconds, or set at a temperature of 250°–300° C. and applied for 20–40 seconds, or set at a temperature of 200°–250° C. and applied for 30–60 seconds. At these elevated temperatures, the transition temperature of approximately 170° C. is exceeded very quickly, and the curing reaction is thus initiated. It has been found that it is precisely a hot air stream which is able to heat a component uniformly even in those areas where undercuts or projections are present, because the stream of hot air can be guided around the component uniformly. It has also been found that it is possible to identify the exact time at which sufficient curing has occurred or at which curing has been completed by visual inspection. That is, toward the end of the curing process, the coating changes its appearance from shiny and colorless to flat and medium-brown. A dark brown-blackish discoloration indicates that the layer has been overheated and has thus become unusable for the purposes of the bond. It is even possible, therefore, to cure individual areas of a component by shifting the hot air from one area to another on the surface, the shift being accomplished only after the required change to a flat, medium-brown color has occurred, which signals that the area in question has cured sufficiently.

As already mentioned, it has been found that it is also possible to see when the individual layers of the two separate preparations have undergone sufficient predrying or precuring. After the first preparation has been applied, it appears visibly wet, and after it has dried partially, it turns a pale white. After this color change to white, the first preparation is ready for the application of the second preparation. The second preparation also looks wet and shiny just after it has been applied, and then after a certain drying time its appearance changes to satiny-to-flat. After the second preparation has reached this state, the final curing operation under the action of heat can be carried out.

An additional advantage which is associated with the process according to the invention and the preparations used for it is that, after the fully cured coating has cooled, it is ready for copolymerization with (meth)acrylate adhesives, (meth)acrylate plastics, or (meth)acrylate composites and remains active in this way for an indeterminate time, as long as it is does not become dirty. This active state means that plastics or composites can be applied to this coating with reproducible adhesion results. Stability tests under room conditions showed that the strength of the bond obtained with substrates prepared with a coating in this way and aged for one month did not differ from that obtained with a test piece which had been coated with plastic immediately after the application of the coating.

The coating process according to the invention could be applied successfully to, or carried out in conjunction with, not only metal carriers as substrates for the coating but also dental and engineering ceramic carriers, including those based on feldspar and on aluminum oxide, as well as thermosets with heat resistance values of more than 180° C. The coating produced by means of the process with the use of the two preparations described above represents an optimum primer layer for a (meth)acrylate adhesive for bonding two substrates together, each of which is provided with the coating.

Additional advantageous features of the process can be found in the subclaims.

In the following, various exemplary embodiments and experimental results are described in detail.

A first example of the production of a coating on metal was carried out as follows:

1. The metal substrate was mechanically cleaned by sandblasting, as a result of which its surface area was increased. The preferred sandblasting agent is aluminum oxide (corundum). The grain size can be in the range of 50–250 μm, and preferably 100–150 μm. Without leading to any significant effect on the quality of the bond obtained subsequently, the blasting pressure can be in the range of as little as 2–5 bars, and preferably 2–3 bars, primarily because of the sensitivity of work involving dental procedures.

2. The surface was roughly dusted off with a hard brush without the use of any auxiliary materials.

3. Preparation I was applied: a water/acetone dispersion of an acrylonitrile/butyl acrylate copolymer and a (meth)acrylate which was nonvolatile at temperatures of up to 250° C., preferably the urethane methacrylate from trimethylhexyl diisocyanate and hydroxyethyl (meth)acrylate (UEDMA).

Sample Formulation 1
- 9 g of copolymer suspension;
- 10 g of distilled water;
- 40 g of acetone, analytical grade; and
- 7 g of UEDMA.

Sample Formulation 2
- 12 g of copolymer suspension;
- 10 g of distilled water;
- 40 g of acetone, analytical grade; and
- 8 g of BisGMA (2,2-bis[p-(2-hydroxy-2-methacryloyloxypropoxy)-phenyl]propane.

Sample Formulation 3
- 6 g of copolymer suspension;
- 10 g of distilled water;
- 40 g of acetone, analytical grade; and
- 3 g of PETA (pentaerythritol tetraacrylate).

A brush was used to apply a thorough coating of Preparation I to the metal body. The coating was then allowed to dry under room conditions for 2–3 minutes until the surface had turned pale white.

4. Preparation II was applied: an acetonic solution of a crosslinking polyurethane baking resin and a (meth)acrylate which was nonvolatile at up to 250° C., preferably the urethane dimethacrylate (UEDMA) from trimethylhexyl diisocyanate and hydroxyethyl (meth)acrylate.

Sample Formulation 4
- 5 g of urethane baking resin solution;
- 2.5 g of UEDMA; and
- 25 g of acetone, analytical grade.

Sample Formulation 5
- 2.5 g of urethane baking resin solution;
- 5 g of BisGMA; and
- 25 g of acetone, analytical grade.

Sample Formulation 6
- 7.5 g of urethane baking resin solution;
- 1.5 g of PETA; and
- 25 g of acetone, analytical grade.

A brush was used to apply a thorough coating of Preparation II. The coating was allowed to dry partially under room conditions for 2–3 minutes until a colorless, satiny-flat surface was observed.

5. The applied layers were then heat-cured at a temperature above 170° C.

6. After the cured layers had cooled, they were ready for copolymerization with (meth)acrylate adhesives, (meth)acrylate plastics, or (meth)acrylate composites.

7. The materials used to test the strength of the bonds were standard commercial filling and facing veneering composites and adhesives from Heraeus Kulzer GmbH, which consisted of inorganic fillers and difunctional and/or polyfunctional (meth)acrylate matrices. The bond strength test was carried out in accordance with Proposed. Standard ISO 10,477, applicable to dental crown and bridge facing materials. The following results were obtained.

Preparation I was applied to the center of an area corresponding to one facing unit (about 100 mm$^2$, approximately 8 mm×12 mm) in an amount such that, after partial drying, 10±1 mg of substance remained and a layer with a thickness of 6±1 μm was produced. Preparation II was applied in a similar thickness, so that the total layer thickness of the uncured coating was 12±1 μm. After the coating had been cured with hot air (see Point 5), 11±1 mg remained with a layer thickness of 7±1 μm. After this layer was joined to the selected plastic, adhesive, or composite, the following bond strength values were obtained in the shear test:

| Bond strength in the shear test; range of results for high-gold and reduced-gold casting alloys, gold alloys for ceramic burn-on and nonnoble metal alloys s/55° C. | After boiling test in water for 30 min at 100° C., MPa | After alternating temperature stress for 5,000 cycles in water: 30 s/5° C.-10 s/RT-30–10 s/RT, MPa |
|---|---|---|
| 1. treatment according to Points 1, 2, 3, 4, 5, 6, 7: DC-Op-DC-Vbm | 18–23 | 17–22 |
| 2. treatment according to Points 1, 2, 4, 3, 5, 6, 7: DC-Op-DC-Vbm: | 5–10 | 3–8 |
| 3. treatment according to Points 1, 2, 3, 4, 5, 6, 7: (ARTG-Op), tooth filling material CHAR | 30–35 | 27–32 |
| 4. treatment according to Points 1, 2, 3, 4, 5, 6, 7: ARTG-Op, ARTG | 33–40 | 30–35 |
| 5. treatment according to Points 1, 2, 3, 4, 5: 300° C. hot air (HA) for 20 s, 6, 7: ARTG-Op-DC-Vbm | 20–25 | 19–24 |

Explanations:
DC-Op: tooth-colored, photocuring, two-component metal topcoat based on (meth)acrylate, 2,2-bis[p-(2-hydroxy-2-methacryloyloxypropoxy)-phenyl] propane (BisGMA), titanium dioxide, and colorizing pigments.
DC-Vbm: tooth-colored, photocuring facing material for dental metal frames based on urethane ethylene glycol dimethacrylate (UEDMA), dodecanediol dimethacrylate (DoDDMA), silicon dioxide, and ground prepolymer.
ART-Op: tooth-colored, photocuring, single-component metal topcoat based on UEDMA, BisGMA, pentaerythritol tetraacrylate ("Penta"), silicon dioxide, titanium dioxide, and colorizing pigments.
ARTG: photocuring polymer glass for dental use based on ultra-finely ground barium-aluminum silicate glass, rheologically active silicic acid, and a mixture of bifunctional and multifunctional (meth)acrylic acid esters.

The table shows that, when the treatment steps explained above are followed, very high bond strengths can be obtained in the shear test. The tests conducted within the scope of alternating temperature stress also show that a permanent, moisture-resistant bond is achieved.

Attention should be drawn in particular to Test 2 in the above summary of the test results. In this test, steps 3 and 4 of the process were reversed; that is, Preparation II was applied and partially dried first, before Preparation I was applied. This reversal of the application sequence of Preparations I and II led to a sharp drop in the adhesion values, which proves that it is absolutely necessary for Preparations I and II to be applied in the sequence according to the invention as explained above.

After optimization and adjustment of the thermal curing parameters to suit the heat capacity of the bond surface, comparable results with respect to the bond formed with (meth)acrylate plastics, (meth)acrylate composites, and (meth)acrylate adhesives were obtained with other metals of a nondental type for nondental uses. Moisture-proof bonds of comparable strength could be achieved even when two metals were bonded to each other by means of appropriate (meth)acrylate adhesives.

We claim:

1. Process for the production of an adhering, moisture-proof coating of plastic on a substrate of metal, ceramic, glass, or polymer comprising:

applying a first preparation to the substrate and allowing said first preparation to at least partially dry;

applying a second preparation to the partially dried first preparation and allowing said second preparation to at least partially dry; and solidifying the coating by heating said coating to a temperature in the range of 150°–400° C.;

the first preparation containing:
5–25 wt. % of an aqueous copolymer suspension, the copolymer consisting of a mixture of 40–80 wt. % of acrylonitrile and 60-20 wt. % of butyl acrylate;
5–20 wt. % of water;
35–75 wt. % of a polar solvent; and
3–15 wt. % of a (meth)acrylate which is nonvolatile at temperatures of up to 250° C., with the provision that the percentages add up to 100%; and the second preparation containing:
5–20 wt. % of a 40–90 wt. % solution of an isocyanate group-free polyurethane heat curing resin in solvent naphtha having a boiling point of about 100 degrees C.;
65–85 wt. % of solvent; and
3–20 wt. % of a (meth)acrylate which is nonvolatile at temperatures of up to 250° C., with the provision that the percentages add up no 100%.

2. Process according to claim 1, wherein the preparation applied first is a preparation which contains an aqueous suspension of acrylonitrile/butyl acrylate copolymer with a solids content of 30–50 wt %.

3. Process according to claim 2, wherein the copolymer of the suspension of the first preparation consists of a mixture of approximately 60 wt. % of acrylonitrile and approximately 40 wt. % of butyl acrylate.

4. Process according to claim 1, wherein the solution used for the second preparation is an approximately 75 wt. % solution of an isocyanate group-free polyurethane heat curing resin in solvent naphtha having a boiling point of about 100 degrees C.

5. Process according to claim 1, wherein ethanol, isopropanol or acetone is used as the solvent in the first preparation and/or the second preparation.

6. Process according to claim 1, wherein the first preparation which is applied contains:
12–18 wt. % of the aqueous copolymer suspension;
14–18 wt. % of water;
50–60 wt. % of acetone; and
7–12 wt. % of (meth)acrylate,
with the provision that the percentages add up to 100%.

7. Process according to claim 1, wherein the second preparation which is applied contains:
8–15 wt. % of polyurethane in solvent naphtha 100;
70–80 wt. % of acetone; and
5–12 wt. % of (meth)acrylate,
with the provision that the percentages add up to 100%.

8. Process according to claim 1, wherein the first and the second preparations are each applied to form a layer with a thickness in the range of 1–10 µm.

9. Process according to claim 1, wherein a stream of hot air is directed at the coating to solidify it.

10. Process according to claim 1, wherein a stream of hot air at a temperature in the range of 200°–400° C. is directed at the coating.

11. Process according to claim 1, wherein the first preparation is applied to a prosthetic component in dentistry such as a bridge, crown, or saddle prosthesis.

12. Process according to claim 11, wherein said coating is applied to a prosthetic dentistry component formed of a noble metal alloy or a nonnoble metal alloy.

13. Process according to claim 1, wherein the substrate is cleaned mechanically or chemically before the first preparation is applied.

14. Process according to claim 1, wherein the (meth)acrylate which the first preparation to be applied contains is a chemical selected from the group consisting of urethane ethylene glycol dimethacrylate (UEDMA), 2,2-bis(p-(2-hydroxy-2-methacryloyloxypropoxy)phenyl)propane (Bis-GMA), and penta-erythritol tetraacrylate (PETA).

15. Process according to claim 1, wherein the (meth)acrylate which the second preparation to be applied contains is a chemical selected from the group consisting of urethane ethylene glycol dimethacrylate (UEDMA), 2,2-bis(p-(2-hydroxy-2-methacryloyloxypropoxy)phenyl)propane (Bis-GMA), and pentaerythritol tetraacrylate (PETA).

16. Process according to claim 1, wherein the second preparation which is applied contains a polyurethane heat curing resin based on a hexamethylene diisocyanate polymer and an oxime.

17. Process according to claim 16, wherein butanone-oxime or caprolactam is used as the oxime.

18. Process according to claim 1, wherein a urethane methacrylate which is formed from trimethylhexyl diisocyanate and hydroxyethyl (meth)acrylate is used.

19. Process of bonding two substrates together, said process comprising:

applying to each of said substrates a respective coating produced according to the process of claim 1 as a primer layer for a (meth)acrylate adhesive; and bonding said two substrates together using said adhesive.

20. Process according to claim 8, wherein said layers have a thickness of 4 to 8 micrometers.

* * * * *